(12) United States Patent
Murakami et al.

(10) Patent No.: US 10,849,496 B2
(45) Date of Patent: Dec. 1, 2020

(54) MOTION SICKNESS ESTIMATION DEVICE, MOTION SICKNESS PREVENTION DEVICE, AND MOTION SICKNESS ESTIMATION METHOD

(71) Applicant: MITSUBISHI ELECTRIC CORPORATION, Tokyo (JP)

(72) Inventors: Takuya Murakami, Tokyo (JP); Yudai Nakamura, Tokyo (JP); Masahiro Naito, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 68 days.

(21) Appl. No.: 16/320,317

(22) PCT Filed: Oct. 5, 2017

(86) PCT No.: PCT/JP2017/036233
§ 371 (c)(1),
(2) Date: Jan. 24, 2019

(87) PCT Pub. No.: WO2018/070330
PCT Pub. Date: Apr. 19, 2018

(65) Prior Publication Data
US 2019/0269321 A1    Sep. 5, 2019

(30) Foreign Application Priority Data
Oct. 11, 2016   (JP) .................................. 2016-199692

(51) Int. Cl.
*A61B 3/11*    (2006.01)
*A61B 3/113*   (2006.01)
(Continued)

(52) U.S. Cl.
CPC ................ *A61B 3/113* (2013.01); *A61B 5/16* (2013.01); *A61B 5/165* (2013.01); *G01M 17/00* (2013.01); *G08G 1/16* (2013.01)

(58) Field of Classification Search
CPC ...................................... A61B 3/113
See application file for complete search history.

(56) References Cited

U.S. PATENT DOCUMENTS 7,043,056 B2 *  5/2006  Edwards ............ G06K 9/00248
                                                    382/103
8,398,546 B2 *  3/2013  Pacione ............. A61B 5/02055
                                                    600/300
(Continued)

FOREIGN PATENT DOCUMENTS

JP       8-247796 A      9/1996
JP    2004-301692 A     10/2004
(Continued)

OTHER PUBLICATIONS

Kitagawa et al. "Method for Reducing Kinetosis Using Viewing Mobile Media in Moving Vehicles", (2013), vol. 67, No. 11, pp. J388-J399.

*Primary Examiner* — Alex C Dunn
(74) *Attorney, Agent, or Firm* — Birch, Stewart, Kolasch & Birch, LLP

(57) ABSTRACT

A motion sickness estimation device includes: a line-of-sight oscillation detector to detect oscillation of a line of sight of an occupant by using an imaging device; an object oscillation detector to detect oscillation of an object located in the line of sight; an oscillation comparator to calculate an oscillation difference from the oscillation of the line of sight and the oscillation of the object; and a motion sickness determiner to determine, on a basis of the oscillation difference, whether the occupant is in a motion sickness state.

8 Claims, 6 Drawing Sheets

(51) Int. Cl.
   *A61B 5/16*   (2006.01)
   *G01M 17/00*  (2006.01)
   *G08G 1/16*   (2006.01)

(56) References Cited

U.S. PATENT DOCUMENTS

| | | | |
|---|---|---|---|
| 2004/0208394 A1 | 10/2004 | Kurata | |
| 2010/0106356 A1* | 4/2010 | Trepagnier | G08G 1/16 701/25 |
| 2015/0081156 A1* | 3/2015 | Trepagnier | G05D 1/0248 701/26 |
| 2015/0294583 A1* | 10/2015 | Pacione | A61B 5/01 434/236 |
| 2016/0022167 A1* | 1/2016 | Simon | A61B 5/14542 600/301 |
| 2016/0262608 A1* | 9/2016 | Krueger | G06T 19/006 |

FOREIGN PATENT DOCUMENTS

| | | |
|---|---|---|
| JP | 2004-317813 A | 11/2004 |
| JP | 2006-34576 A | 2/2006 |
| JP | 2007-236644 A | 9/2007 |
| JP | 2008-120271 A | 5/2008 |
| JP | 2011-83379 A | 4/2011 |
| JP | 2014-21783 A | 2/2014 |

* cited by examiner

MOTION SICKNESS ESTIMATION DEVICE, MOTION SICKNESS PREVENTION DEVICE, AND MOTION SICKNESS ESTIMATION METHOD

TECHNICAL FIELD

The present invention relates to a device and method for estimating motion sickness of an occupant in a conveyance.

BACKGROUND ART

From old times, occupants who read documents, such as newspapers or books, or watch images through displays in moving vehicles have been troubled by motion sickness resulting from being subjected to vibration of the vehicles due to the road surface conditions, engines, rail joints, or the like. Motion sickness is also called "kinetosis" or "acceleration sickness", and is an autonomic response caused by vibration, in particular irregular repetition of acceleration and deceleration, stimulating the semicircular canals and vestibule of each inner ear. To prevent motion sickness, occupants have taken measures, such as looking in the distance through a window or taking anti-motion sickness drugs.

It is thought that motion sickness also occurs when a conflict occurs between body balance sense information obtained from the human semicircular canals and visual information obtained by the human eyes. Based on this, studies have been conducted that aim to resolve symptoms of motion sickness by showing an occupant an image consistent with the balance sense information (see Non Patent Literature 1).

As a method for preventing motion sickness, there has been proposed a method that makes it possible to prevent motion sickness by estimating motion sickness of an occupant on the basis of an integral value of the acceleration of the vehicle or the acceleration of the head of the occupant and controlling the vehicle to reduce the acceleration of the head of the occupant. Since it is difficult to attach a sensor to the head, the acceleration of the head has been estimated from posture data, a pressure distribution, and the like (see Patent Literature 1).

CITATION LIST

Patent Literature

Patent Literature 1: Japanese Patent Application Publication No. 2007-236644 (pages 4-6 and FIG. 2)

Non Patent Literature 1: Etsuji Kitagawa, "Research and Development on System for Reducing Kinetosis in Using Media in Conveyance," The Journal of The Institute of Image Information and Television Engineers, Vol. 67, No. 11, pp. J388-J399, 2013

SUMMARY OF INVENTION

Technical Problem

However, the technique against motion sickness as in Patent Literature 1 only detects the acceleration of the head. This technique cannot compensate a difference, which is one of the causes of motion sickness, between oscillation of the line of sight due to vestibulo-ocular reflex or optokinetic nystagmus and oscillation of an object located in the line of sight, and cannot detect vestibulo-ocular reflex. Also, in the method of Non Patent Literature 1, it is necessary to force special actions on the occupant, such as force the occupant to watch a terminal while limiting the viewing conditions, such as the distance to the terminal.

The "vestibulo-ocular reflex" is a reflex function in which the line of sight moves in a direction opposite to a direction in which the head is accelerated. For example, a function in which when a head is tilted up during looking ahead, the line of sight involuntarily moves downward is vestibulo-ocular reflex. When the view remains unchanged while the semicircular canals sense acceleration on a watercraft or in a train, a conflict occurs between balance sense information and visual information, causing motion sickness.

The "optokinetic nystagmus" refers to an oscillation state of the eyeballs caused by repetition of slow eyeball movement and fast eyeball movement. It occurs, for example, in looking out of a window of a train or in similar situations, due to alternation of a slow eye movement that follows an object sequentially passing before the eyes and a fast movement in the opposite direction that tries to catch the next object. Optokinetic nystagmus causes abnormal actions of the extraocular muscles. It is thought that nerve signals caused by the actions stimulate the medulla oblongata, which controls the autonomic nervous system, through the vestibular nerves and disrupt its function, causing symptoms such as nausea.

The present invention has been made to solve the problems as described above, and is intended to provide a motion sickness estimation device capable of accurately estimating motion sickness by detecting oscillation of a line of sight without having to force a special action, such as watching a terminal, on an occupant.

Solution to Problem

To achieve the above object, according to the present invention, there are provided a line-of-sight oscillation detector to detect oscillation of a line of sight of an occupant, an object oscillation detector to detect oscillation of an object located in the line of sight, an oscillation comparator to calculate an oscillation difference from the oscillation of the line of sight and the oscillation of the object, and a motion sickness determiner to determine, on a basis of the oscillation difference, whether the occupant is in a motion sickness state.

Advantageous Effects of Invention

With this configuration, it is possible to provide a motion sickness estimation device that has no need to force a special action, such as watching a terminal, on an occupant, by the line-of-sight oscillation detector detecting oscillation of a line of sight of the occupant in a conveyance, the object oscillation detector detecting oscillation of an object located in the line of sight of the occupant, the oscillation comparator calculating an oscillation difference from the oscillation of the line of sight and the oscillation of the object, and the motion sickness determiner determining, on a basis of the oscillation difference, whether the occupant is in a motion sickness state.

DESCRIPTION OF EMBODIMENTS

First Embodiment

Figure 1:
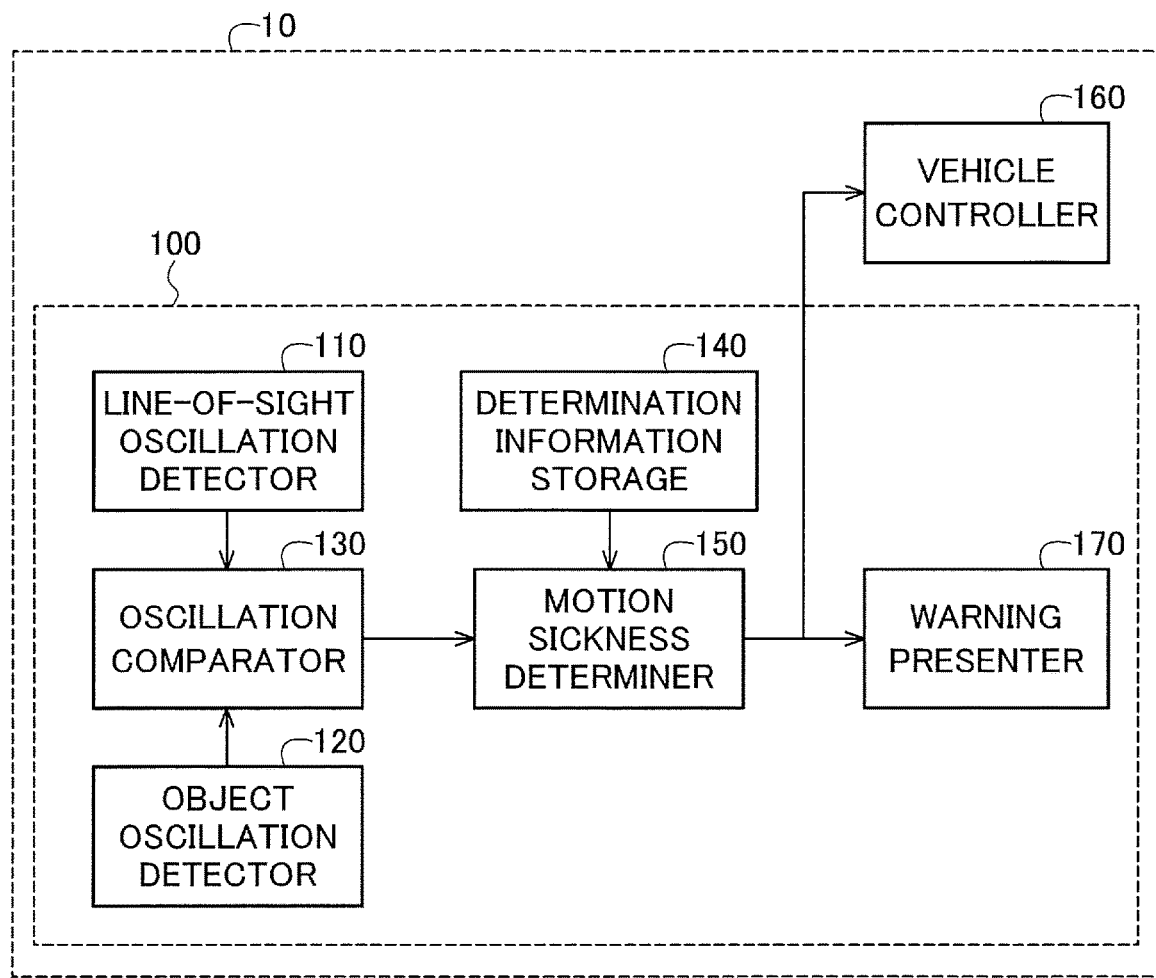
FIG. 1 is a block diagram illustrating a configuration of a motion sickness prevention device including a motion sickness estimation device according to a first embodiment of the present invention.

FIG. 1 is a block diagram illustrating a configuration of a motion sickness prevention device including a motion sickness estimation device according to a first embodiment. A motion sickness prevention device 10 includes a motion sickness estimation device 100 and a vehicle controller 160. The motion sickness estimation device 100 includes a line-of-sight oscillation detector 110, an object oscillation detector 120, an oscillation comparator 130, a determination information storage 140, a motion sickness determiner 150, and a warning presenter 170. The line-of-sight oscillation detector 110 detects oscillation of a line of sight of an occupant. The object oscillation detector 120 detects oscillation of an object at which the occupant is looking. The oscillation comparator 130 compares the amount of oscillation of the line of sight that is an output of the line-of-sight oscillation detector 110 and the amount of oscillation of the object located in the line of sight that is an output of the object oscillation detector 120. The determination information storage 140 stores a threshold value of an oscillation difference that can lead to motion sickness. Here, the oscillation difference that can lead to motion sickness is a difference between the amount of oscillation of the line of sight that is an output of the line-of-sight oscillation detector 110 and the amount of oscillation of the object located in the line of sight that is an output of the object oscillation detector 120. Here, the threshold value is the value of the oscillation difference above which motion sickness can be caused. In other words, the threshold value is the value of the oscillation difference at or below which motion sickness will not be caused. The motion sickness determiner 150 compares an output of the oscillation comparator 130 with the threshold value of the determination information storage 140 and determines a motion sickness state. The vehicle controller 160 controls the vehicle on the basis of a determination result output by the motion sickness determiner 150. The warning presenter 170 issues a warning to the occupant and prompts the occupant to take a rest, on the basis of the determination result output by the motion sickness determiner 150. The warning may be a warning using a sound through a speaker, or may be a warning using an image displayed on an in-vehicle display, a head-up display (HUD), an instrument panel, or the like. The "head-up display (HUD)" is a display that directly displays information in the field of view of a person by projecting an image onto a transparent optical glass element or other methods. The "instrument panel" is a control panel located in front of a driver's seat of an automobile.

In the line-of-sight oscillation detector 110, to detect oscillation of the line of sight, movement of the position of the iris in an imaged eye is detected as the oscillation. The "oscillation of the line of sight" is oscillation of a visual axis that is a line connecting a center of an eye and a target being viewed, and is a phenomenon caused by oscillation of the target being viewed. Methods for detecting oscillation of the line of sight include electrooculography, the optical lever method, the search coil method, the limbus tracking method, the corneal reflection method, and the like. The "electrooculography" focuses on the fact that change in voltage of an eyeball is substantially proportional to the rotation angle of the eyeball, and places skin electrodes around the eye and measures movement of the eyeball from change in voltage of the eyeball. The "optical lever method" is a method that places a contact lens with a small mirror attached to its edge on the cornea and extracts reflected light resulting from reflection of a light beam by the mirror by using image analysis or photoelectric conversion. The "search coil method" is a method that attaches coils to the edge of a contact lens, places a person wearing the lens in a uniform alternating magnetic field, and extracts an induced current that is proportional to rotation of the eyeball, thereby detecting the line-of-sight oscillation. The "limbus tracking method" is a method that measures eyeball movement by radiating weak infrared light to the boundary between the iris and the sclera and detecting the resulting reflected light with a sensor. The "corneal reflection method" is a method that measures eyeball movement on the basis of the position of a corneal reflection image that brightly appears when the cornea is illuminated with illumination light from a point light source. The present invention does not require attaching an object for measurement to the eyeball as described above.

The present invention detects oscillation of the line of sight by imaging line-of-sight oscillation of the occupant. In detecting oscillation of the line of sight, the iris is detected in an imaged eye, for example. Then, it is detected whether the boundary between the position of the iris and the position of a part, such as the sclera, outside the iris is moving over time. When it is moving, it is determined that there is line-of-sight oscillation. For example, when change in frequency of movement of a moving position of the boundary is large, it can be determined that the oscillation amount is large. In detecting the direction of the oscillation, it is possible to take, as a reference, the mounting direction in which a camera for imaging line-of-sight oscillation of the occupant is mounted. It is also possible to attach an acceleration sensor to a camera for imaging line-of-sight oscillation of the occupant and detect a displacement of the camera from a vertical direction. As above, it is possible to match the reference of the direction of the detection of the line-of-sight oscillation by imaging with the camera and the reference of the direction of the detection of oscillation of the object by an acceleration sensor.

Figure 2:
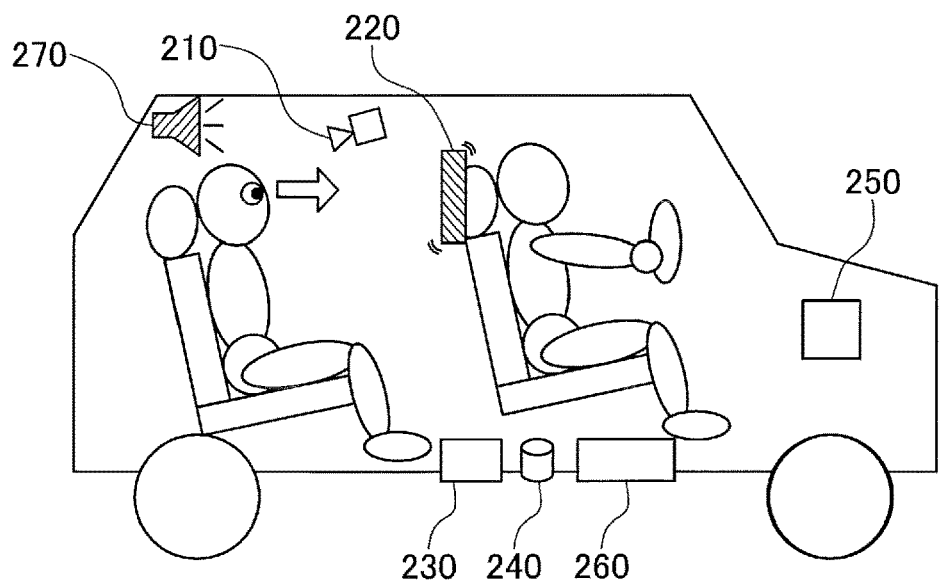
FIG. 2 is an explanatory diagram illustrating an arrangement of elements in a vehicle including the motion sickness prevention device according to the first embodiment of the present invention.

FIG. 2 is an explanatory diagram illustrating an arrangement of elements in the vehicle including the motion sickness prevention device according to the first embodiment of the present invention. In the vehicle illustrated in FIG. 2, an in-vehicle camera 210, an in-vehicle display 220 with an acceleration sensor attached thereto, an oscillation comparator 230, a storage device 240, a determiner 250, a conveyance controller 260, and a speaker 270 are arranged. The correspondence relationship between the elements in FIG. 2 and the elements in FIG. 1 is as follows: The in-vehicle camera 210 corresponds to the line-of-sight oscillation detector 110. The in-vehicle display 220 with the acceleration sensor attached thereto corresponds to the object oscillation detector 120. The oscillation comparator 130 corresponds to the oscillation comparator 230. The storage device 240 corresponds to the determination information storage 140. The determiner 250 corresponds to the motion sickness determiner 150. The conveyance controller 260 corresponds to the vehicle controller 160. The speaker 270 corresponds to the warning presenter 170.

The in-vehicle camera 210 is a device that obtains line-of-sight oscillation of an occupant, which is a detection target, by imaging. The in-vehicle camera 210 is connected to the oscillation comparator 230. The camera illustrated in FIG. 2 may be connected through wiring, such as wire harness, or may be connected wirelessly. The camera may be a common RGB camera, or may be an IR camera. The "RGB camera" is a camera that communicates signals of three colors of red, green, and blue through three different cables or the like, and typically uses three independent CCD sensors. The "IR camera" is an infrared camera, and a camera sensitive to wavelengths in the infrared region.

In FIG. 2, the acceleration sensor is provided to the in-vehicle display 220, which is assumed to be viewed by the occupant for a long time. Since the in-vehicle display 220 is located near the occupant, the apparent amount of movement thereof due to vibration is large compared to a distant object, and thus the above-described difference from the oscillation of the line of sight is large. Thus, watching the in-vehicle display 220 is likely to cause motion sickness. Also, it is easy to directly attach the acceleration sensor to the in-vehicle display 220. From the above, by attaching the acceleration sensor to the in-vehicle display 220, it is possible to accurately measure the oscillation and use it for motion sickness estimation. The position where the acceleration sensor is mounted is not limited to the in-vehicle display 220.

The oscillation comparator 230 in FIG. 2 compares the line-of-sight oscillation detected by the in-vehicle camera 210 and the oscillation detected by the acceleration sensor provided in the in-vehicle display 220. By calculating a difference between the line-of-sight oscillation detected by the in-vehicle camera 210 and the oscillation detected by the acceleration sensor provided in the in-vehicle display 220, a component of vestibulo-ocular reflex, which causes motion sickness, is extracted. It is possible to time-integrate the difference, thereby providing motion sickness estimation with reduced effect of noise.

The speaker 270 illustrated in FIG. 2 is provided to, when the oscillation difference obtained from the oscillation comparator 230 exceeds the threshold value, determine that it is oscillation leading to motion sickness, and issue a warning to the occupant. The motion sickness determination of the present invention is a determination that there is an indication of motion sickness, and the determination is made from the environment around the occupant, regardless of whether the occupant is aware of being in a motion sickness state.

The conveyance controller 260 illustrated in FIG. 2 reduces the oscillation difference obtained from the oscillation comparator 230. For example, the conveyance controller 260 adjusts a suspension of a seat on which the occupant is sitting, to reduce sway of the person. The "suspension" of the seat of the vehicle has a function as a shock absorber that prevents the unevenness of the road surface from being transmitted to the vehicle body, and is a mechanism that improves ride quality, handling stability, or the like. The conveyance controller 260 also adjusts a suspension of a seat supporting the in-vehicle display. The conveyance controller 260 also performs deceleration to reduce sway. The conveyance controller 260 also presents a route with a good road surface condition by cooperating with a car navigation system. The conveyance controller 260 also presents a point where it is possible to take a rest.

To enhance the effect of reducing motion sickness of the present invention, it is possible to change the environment in the vehicle, thereby reducing the occurrence of motion sickness of the occupant or reducing the degree of motion sickness. For example, changing the environment in the vehicle includes diffusing a fragrance substance into the vehicle. Also, changing the environment in the vehicle includes playing music for the purpose of relaxing the occupant or for other purposes. Also, changing the environment in the vehicle includes opening or closing a window for the purpose of exposing the occupant to the outside air or for other purposes. Also, changing the environment in the vehicle includes adjusting an air conditioner for the purpose of making the occupant comfortable or for other purposes. Also, changing the environment in the vehicle includes changing the restraining state of the seat belt for the purpose of preventing the occupant from feeling pressure or for other purposes.

Although the above description has described the present invention as being implemented by hardware, part or all of the signal processing illustrated in FIG. 1 can be implemented by software or a programmed computer.

Figure 3:
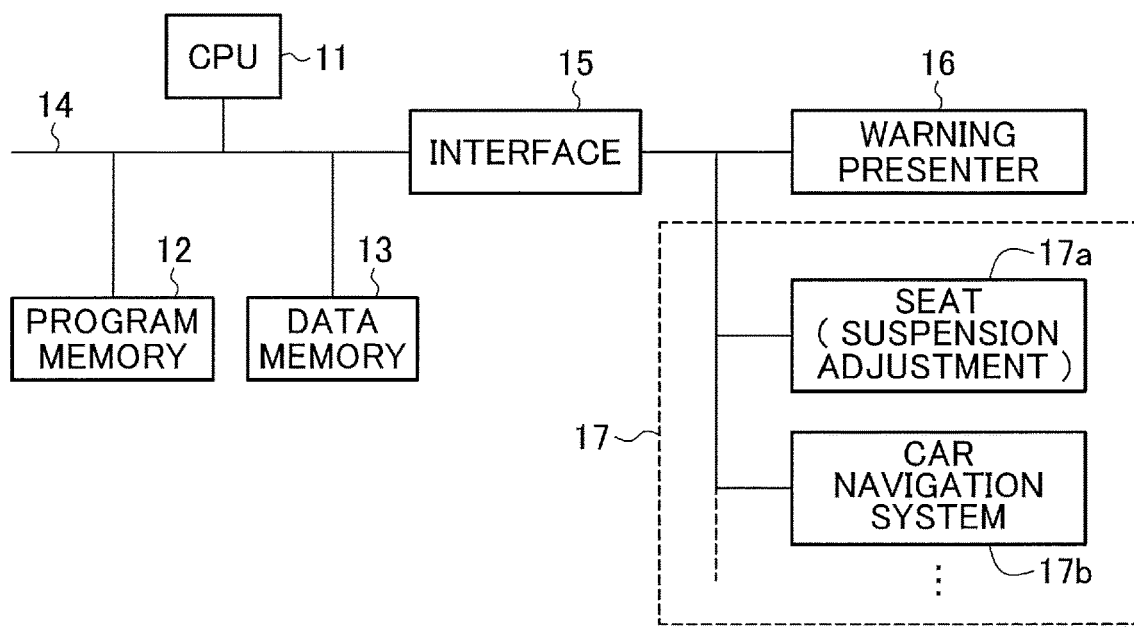
FIG. 3 is a block diagram illustrating another configuration of the motion sickness prevention device according to the first embodiment of the present invention.

FIG. 3 is a block diagram illustrating another configuration of the motion sickness prevention device according to the first embodiment of the present invention. The illustrated motion sickness estimation device includes a CPU 11, a program memory 12, a data memory 13, a bus 14 that connects these, an interface 15, and a warning presenter 16. The "CPU", which is an abbreviation for Central Processing Unit, is a device that performs calculation or control.

The CPU 11 operates according to a program stored in the program memory 12. It stores various data items into the data memory 13 during the process of the operation. An estimation result is supplied to the warning presenter 16 through the interface 15. The estimation result is also supplied to an operation section 17 of the vehicle through the interface 15. The operation section 17 is, for example, a suspension adjustment 17a of a seat. The operation section 17 is a car navigation system 17b. The operation section 17 is constituted by the suspension adjustment or car navigation system, and may be constituted by one or both of them. The operation section 17 corresponds to the vehicle controller 160 or conveyance controller 260 in the above description.

Hereinafter, the process performed by the CPU 11 will be described with reference to FIG. 4.

Figure 4:
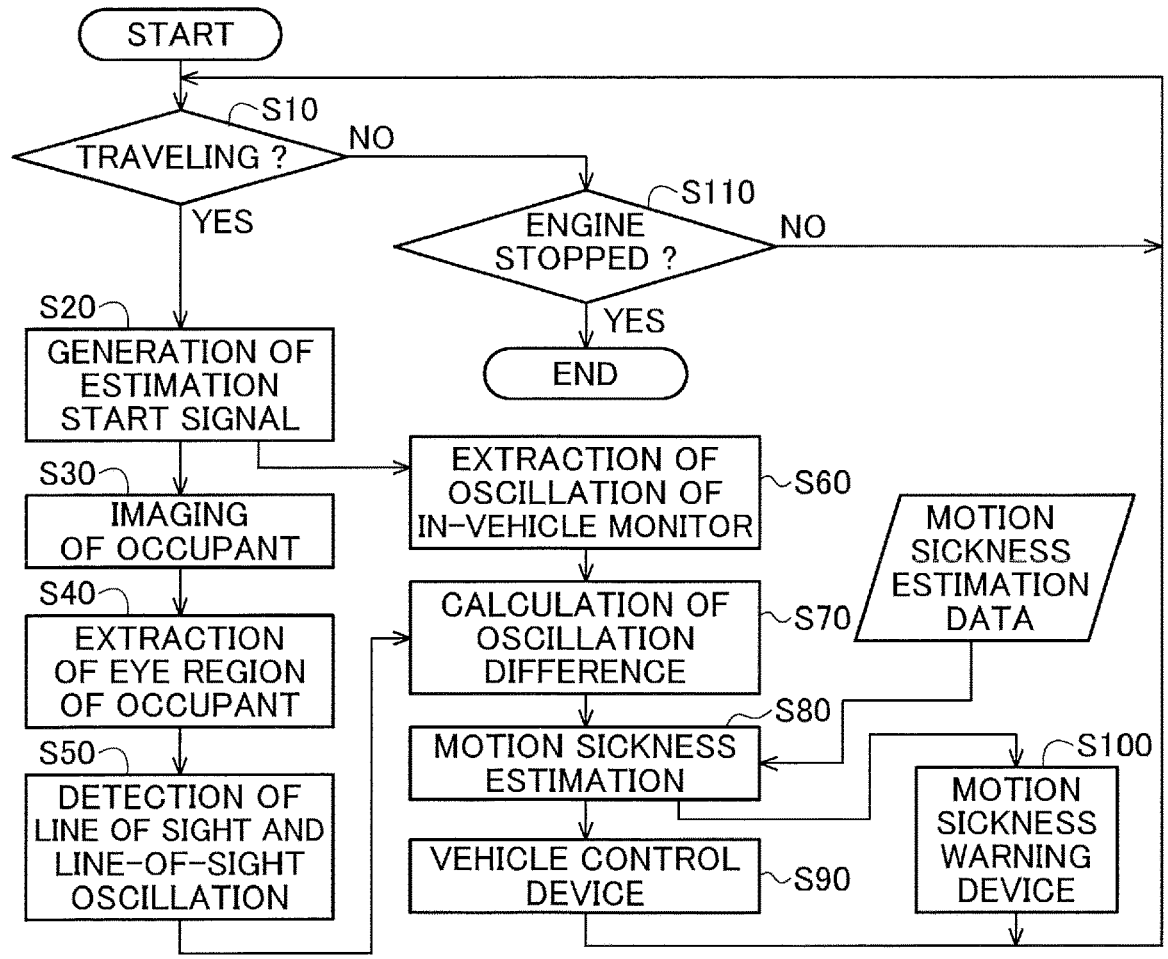
FIG. 4 is a flowchart illustrating a motion sickness estimation method according to the first embodiment of the present invention.

FIG. 4 is a flowchart illustrating a motion sickness estimation method according to the first embodiment of the present invention. The motion sickness estimation method illustrated in FIG. 4 includes a traveling determination step S10, an estimation start signal generation step S20, an imaging step S30, a region extraction step S40, a line-of-sight oscillation detection step S50, an object oscillation detection step S60, an oscillation comparison step S70, a motion sickness estimation step S80, a vehicle control step S90, a motion sickness warning step S100, and an engine stop determination step S110.

The traveling determination step S10 determines whether the vehicle is in a traveling state. The determination is made by acquiring determination as to whether the vehicle is traveling from CAN information or the like. The "CAN", which is an abbreviation for Controller Area Network, is a network standard for connecting an electronic circuit and devices that has been developed as a communication technique between in-vehicle devices.

When it is determined that the vehicle is in a traveling state, in the estimation start signal generation step S20, an estimation start signal is generated by a head unit and supplied to the in-vehicle camera 210 and an illumination associated therewith. "Head unit" is a general term for units that control audio devices, car navigation systems, or the like. Next, in the imaging step S30, the in-vehicle camera 210, which has received the supplied signal, images an occupant.

In the region extraction step S40, a device associated with the in-vehicle camera 210 extracts a region of an eye of the occupant. In the line-of-sight oscillation detection step S50, the line of sight and its oscillation are detected from the image of the detected eye region. The result of the line-of-sight oscillation detection step S50 is sent to the oscillation comparison step S70. On the other hand, when it is determined in the traveling determination step S10 that the vehicle is not in a traveling state, in the engine stop determination step S110, it is determined whether the engine is in a stopped state. When the vehicle is traveling, the motion sickness estimation is continued; when the vehicle is stopped, the estimation is not performed. When the vehicle is in a stopped state and the engine is also in a stopped state, the estimation ends.

After the estimation as to whether motion sickness is being experienced is started at the estimation start signal generation step S20, in the in-vehicle monitor oscillation extraction step S60, oscillation of the in-vehicle monitor is extracted. In the oscillation comparison step S70, an oscillation difference is calculated from the oscillation of the line of sight resulting from the line-of-sight oscillation detection step S50 and the oscillation of the in-vehicle monitor resulting from the in-vehicle monitor oscillation extraction step S60. In the motion sickness estimation step S80, a motion sickness estimation is made from the oscillation difference on the basis of motion sickness estimation data. In the vehicle control step S90, the operation section of the vehicle is controlled on the basis of the result of the motion sickness estimation. Also, in the motion sickness warning step S100, a motion sickness warning is issued on the basis of the result of the motion sickness estimation. Then, the above flow is repeated by returning to the traveling determination step S10.

The above has described the operations of the motion sickness estimation device and motion sickness estimation method. With the above configuration, by detecting the state of an occupant in a conveyance and oscillation of an object located in the line of sight of the occupant and comparing their oscillations by the estimation means, it is possible to estimate the motion sickness state of the occupant. Further, by the vehicle controller controlling the vehicle on the basis of the estimation result, it is possible to prevent motion sickness of the occupant.

Second Embodiment

Figure 5:
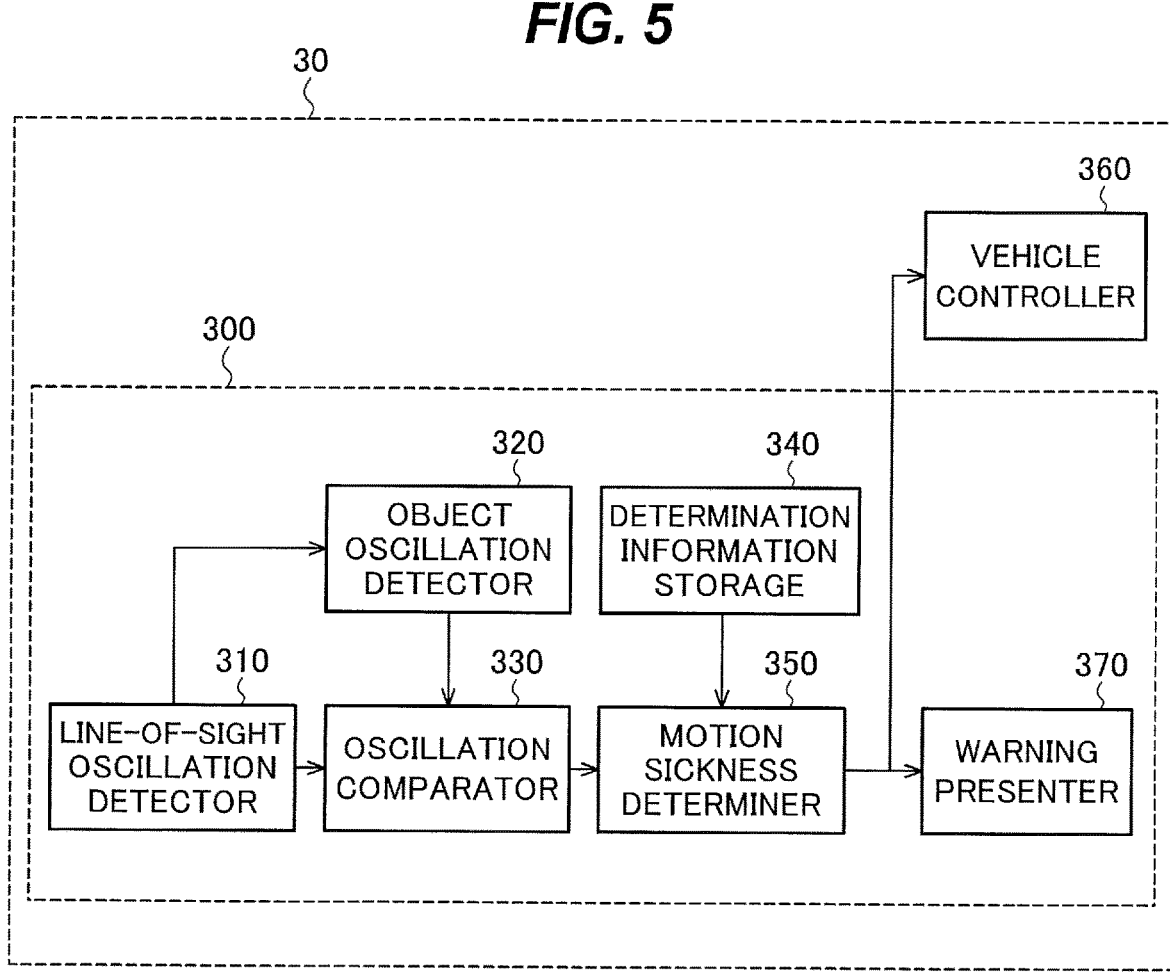
FIG. 5 is a block diagram illustrating a configuration of a motion sickness prevention device including a motion sickness estimation device according to a second embodiment of the present invention.

FIG. 5 is a block diagram illustrating a configuration of a motion sickness prevention device including a motion sickness estimation device according to a second embodiment. A motion sickness prevention device 30 includes a motion sickness estimation device 300 and a vehicle controller 360. The motion sickness estimation device 300 includes a line-of-sight oscillation detector 310, an object oscillation detector 320, an oscillation comparator 330, a determination information storage 340, a motion sickness determiner 350, and a warning presenter 370. The line-of-sight oscillation detector 310 detects a line of sight of an occupant and oscillation of the line of sight. The object oscillation detector 320 images an object located in the line of sight detected by the line-of-sight oscillation detector 310 and detects oscillation of the object. The oscillation comparator 330 compares the amount of the oscillation of the line of sight that is an output of the line-of-sight oscillation detector 310 and the amount of the oscillation of the object located in the line of sight that is an output of the object oscillation detector 320. An oscillation difference calculated by the oscillation comparator 330 is input into the motion sickness determiner 350. The motion sickness determiner 350 performs motion sickness determination on the basis of a comparison of the oscillation difference with a threshold value from the determination information storage 340. The threshold value is the value of the oscillation difference above which motion sickness can be caused, as described in the first embodiment. The vehicle controller 360 controls the vehicle on the basis of the determination result output by the motion sickness determiner 350. The warning presenter 370 issues a warning to the occupant and prompts the occupant to take a rest or other actions, on the basis of the determination result output by the motion sickness determiner 350. The warning may be an audible warning or a visual warning, as in the first embodiment.

Figure 6:
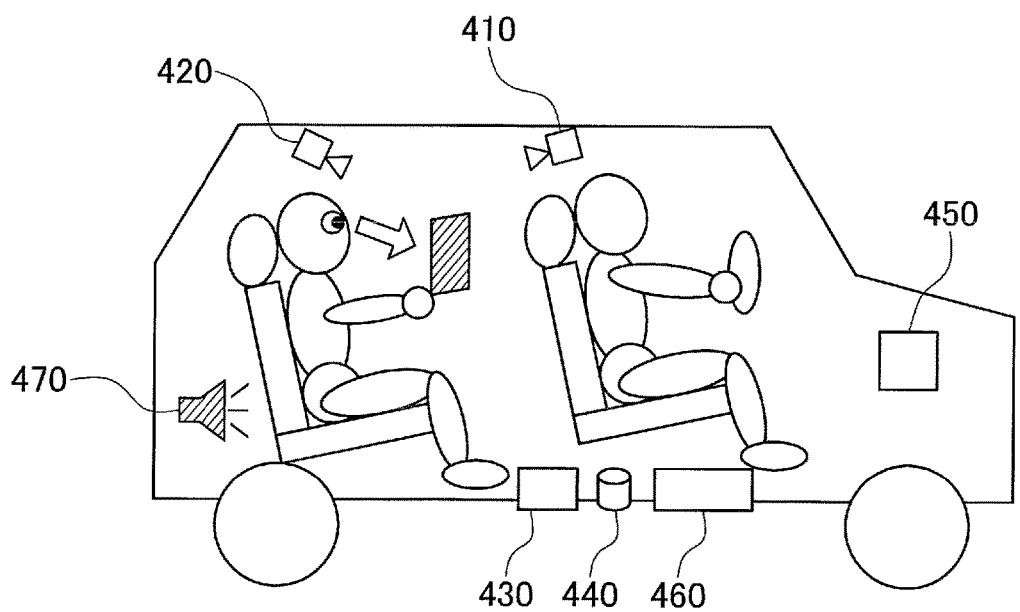
FIG. 6 is an explanatory diagram illustrating an arrangement of elements in a vehicle including the motion sickness prevention device according to the second embodiment of the present invention.

FIG. 6 is an explanatory diagram illustrating an arrangement of elements in the vehicle including the motion sickness prevention device according to the second embodiment of the present invention. In the vehicle illustrated in FIG. 6, an in-vehicle camera (for detecting a line of sight) 410, an in-vehicle cameras (for imaging an object in the line of sight) 420, an oscillation comparator 430, a storage device 440, a determiner 450, a conveyance controller 460, and a speaker 470 are arranged. The correspondence relationship between the elements in FIG. 6 and the elements in FIG. 5 is as follows: The in-vehicle camera 410 corresponds to the line-of-sight oscillation detector 310. The in-vehicle camera (for imaging an object in the line of sight) 420 corresponds to the object oscillation detector 320. The oscillation comparator 430 corresponds to the oscillation comparator 330. The storage device 440 corresponds to the determination information storage 340. The determiner 450 corresponds to the motion sickness determiner 350. The conveyance controller 460 corresponds to the vehicle controller 360. The speaker 470 corresponds to the warning presenter 370.

The in-vehicle camera 410 is a device that obtains line-of-sight oscillation of an occupant, which is a detection target, by imaging the occupant. The in-vehicle camera 410 is connected to the oscillation comparator 430. The in-vehicle camera 420 is also connected to the oscillation comparator 430.

The in-vehicle camera 420 is one or more cameras located inside or outside the vehicle. The in-vehicle camera 420 determines an object located in the line of sight of the occupant obtained by the in-vehicle camera 410, and obtains oscillation of the object from an imaged image. The determination of the object located in the line of sight obtained by the in-vehicle camera 410 may be based on the position of a pupil. Alternatively, the determination of the object located in the line of sight may be based on the orientation of the face. Alternatively, the determination of the object located in the line of sight may be made by reference to an image reflected on an eye. Since it is possible to make a comparison with oscillation of an arbitrary object, it is possible to estimate motion sickness of an occupant reading a book or an occupant operating a mobile phone, for example. The in-vehicle camera 410 and in-vehicle camera 420 may be connected through wiring, such as wire harness, or may be connected wirelessly.

The oscillation comparator 430 compares the line-of-sight oscillation detected by the in-vehicle camera 410 and the oscillation of the object located in the line of sight obtained from the in-vehicle camera 420. The oscillation comparator 430 calculates a difference between the oscillations, thereby extracting oscillation due to vestibulo-ocular reflex.

The determination information storage 440 stores one or more threshold values used in performing motion sickness determination from the oscillation difference output by the oscillation comparison device 430.

The motion sickness estimation device 450 can determine the degree of the motion sickness by comparing the oscillation difference output by the oscillation comparison device 430 with the one or more threshold values, corresponding to degrees of motion sickness, in the determination information storage device 440.

The conveyance controller 460 reduces the oscillation difference obtained from the oscillation comparator 430. For example, the conveyance controller 460 adjusts a suspension of a seat on which the occupant is sitting, to reduce sway of the person. The conveyance controller 460 also performs deceleration to reduce sway. The conveyance controller 460 also presents a route with a good road surface condition by cooperating with a car navigation system. The conveyance controller 460 also presents a point where it is possible to take a rest.

When the oscillation difference obtained from the oscillation comparator 430 exceeds a threshold value, the speaker 470 determines that it is an oscillation leading to motion sickness, and issues a warning to the occupant. It is also possible that a portion, such as the oscillation comparator 430, connected to the speaker 470 determines, from a comparison of the oscillation difference with the threshold value, that it is an oscillation leading to motion sickness, and the determination result is sent to the speaker 470.

Although the above has described implementation by hardware, implementation by software will be described.

As described for the motion sickness estimation method of the first embodiment, a motion sickness estimation device for executing software of a motion sickness estimation method is illustrated by FIG. 3 as described in the first embodiment; hereinafter, a process performed by the CPU 11 will be described with reference to FIG. 7.

Figure 7:
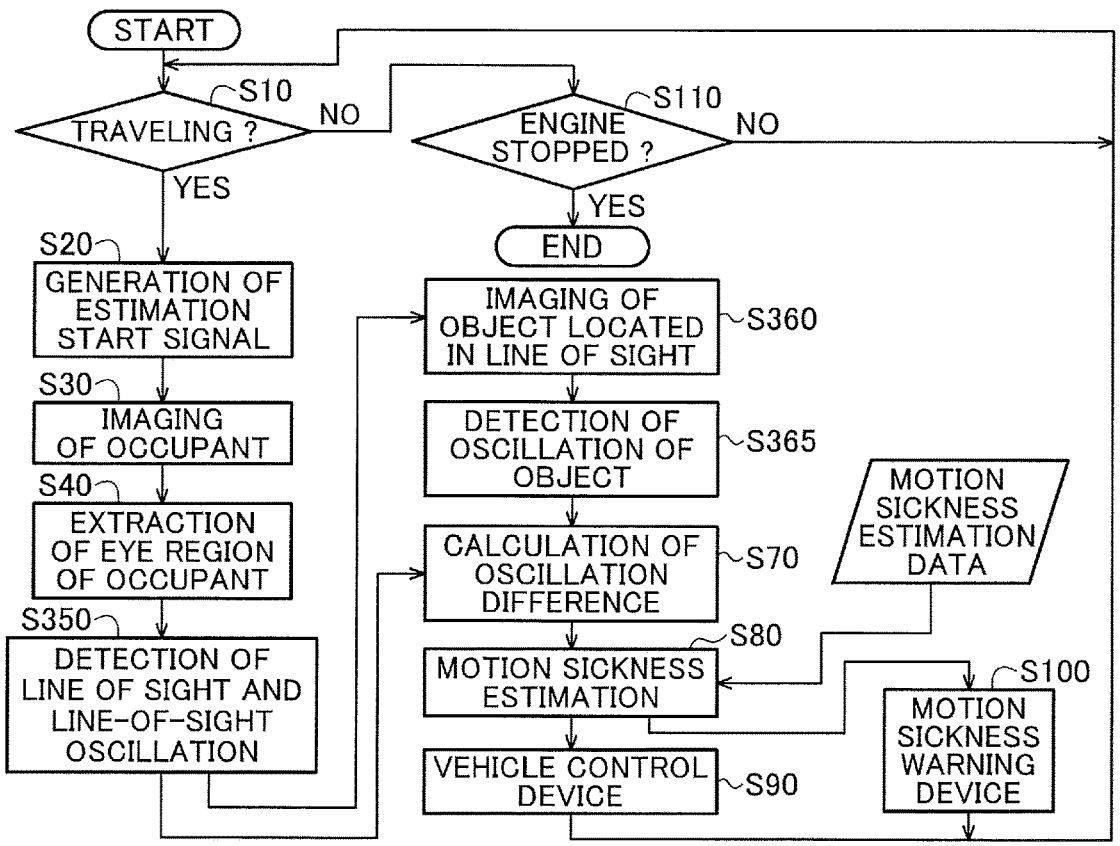
FIG. 7 is a flowchart illustrating a motion sickness estimation method according to the second embodiment of the present invention.

FIG. 7 is a flowchart illustrating the motion sickness estimation method according to the second embodiment of the present invention. The motion sickness estimation method illustrated in FIG. 7 includes a traveling determination step S10, an estimation start signal generation step S20, an imaging step S30, a region extraction step S40, a line-of-sight oscillation detection step S350, an object imaging step S360, an object oscillation detection step S365, an oscillation comparison step S70, a motion sickness estimation step S80, a vehicle control step S90, a motion sickness warning step S100, and an engine stop determination step S110. For the reference characters of the steps of FIG. 7, the same reference characters are assigned to the steps that perform the same operations as those in the first embodiment.

The traveling determination step S10 determines whether the vehicle is in a traveling state. When it is determined that the vehicle is in a traveling state, in the estimation start signal generation step S20, an estimation as to whether motion sickness is being experienced is started. On the other hand, when it is determined in the traveling determination step S10 that the vehicle is not in a traveling state, in the engine stop determination step S110, it is determined whether the engine is in a stopped state. When the vehicle is traveling, the motion sickness estimation is continued; when the vehicle is stopped, the estimation is not performed. When the vehicle is in a stopped state and the engine is also in a stopped state, the estimation ends. When the estimation as to whether motion sickness is being experienced is started, an occupant is then imaged in the imaging step S30.

In the region extraction step S40, a region of an eye of the occupant is extracted. In the line-of-sight oscillation detection step S350, the line of sight and line-of-sight oscillation are detected from the image of the eye region of the occupant. The result of the line-of-sight oscillation detection step S350 is sent to the object imaging step S360 and oscillation comparison step S70.

In the object imaging step S360, on the basis of the line-of-sight information of the occupant, an object located in the line of sight is determined and imaged. In place of the camera, it is possible to form a LIDAR or an interferometer including a laser light source and thereby detect the oscillation from reflected light from an oscillating or vibrating object. The "LIDAR", which is an abbreviation for Laser Imaging Detection and Ranging, is a remote sensing technique that measures scattered light resulting from illumination with pulsed laser light and analyze a distance to a distant target or properties of the target.

In the object oscillation detection step S365, oscillation of the object in the line of sight is detected. Oscillation of the target object in an input image is detected. The oscillation may be detected using an image imaged by a camera, or may be detected from information obtained by ranging with laser.

In the oscillation comparison step S70, an oscillation difference is calculated from the oscillation of the line of sight and the oscillation of the object in the line of sight. In the motion sickness estimation step S80, a motion sickness estimation is performed from the oscillation difference on the basis of motion sickness estimation data. In the vehicle control step S90, the vehicle is controlled on the basis of the result of the motion sickness estimation. Also, in the motion sickness warning step S100, a warning of being in a motion sickness state is issued on the basis of the result of the motion sickness estimation. Then, the above flow is repeated by returning to the traveling determination step S10.

The above has described the operations of the motion sickness estimation device and motion sickness estimation method of the second embodiment. The motion sickness estimation device and motion sickness estimation method of the second embodiment provide the same advantages as the motion sickness estimation device and motion sickness estimation method of the first embodiment.

Third Embodiment

Figure 8:
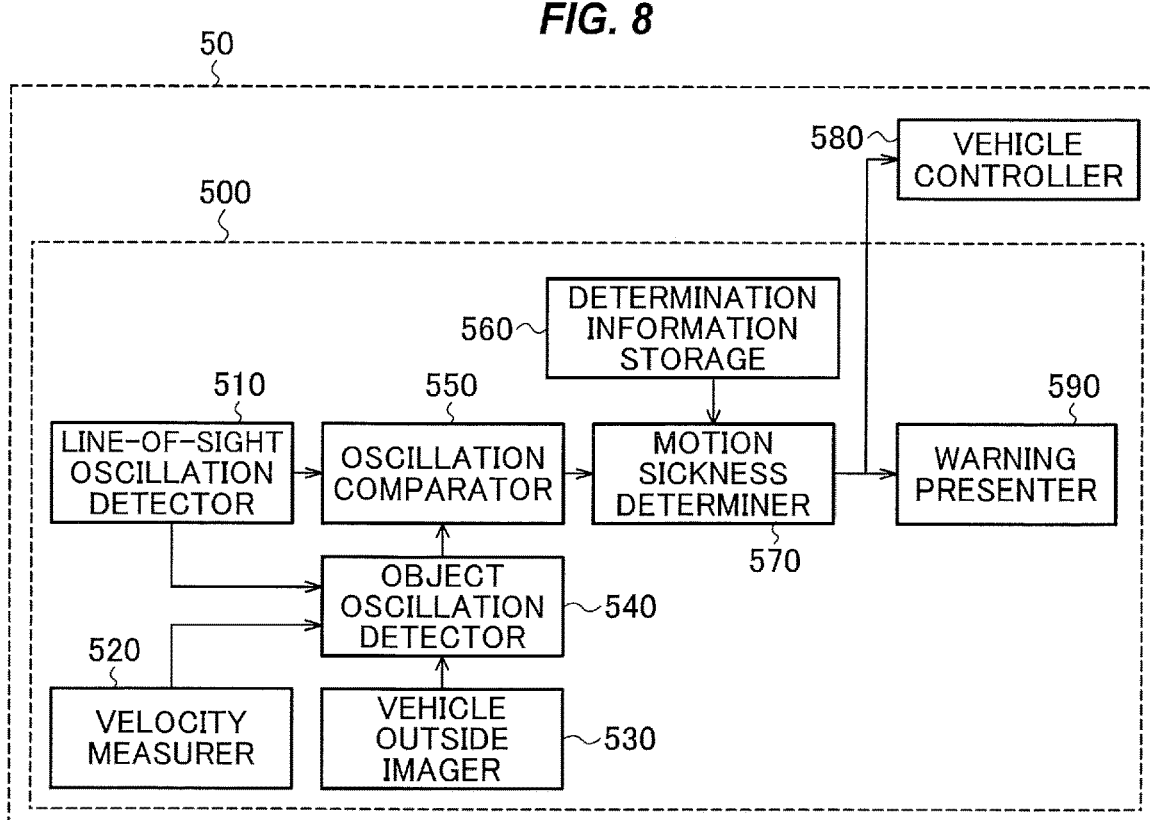
FIG. 8 is a block diagram illustrating a configuration of a motion sickness prevention device including a motion sickness estimation device according to a Gccond third embodiment of the present invention.

FIG. 8 is a block diagram illustrating a configuration of a motion sickness prevention device including a motion sickness estimation device according to a third embodiment. A motion sickness prevention device 50 includes a motion sickness estimation device 500 and a vehicle controller 580. The motion sickness estimation device 500 includes a line-of-sight oscillation detector 510, a velocity measurer 520, a vehicle outside imaging detector 530, an object oscillation detector 540, an oscillation comparator 550, a determination information storage 560, a motion sickness determiner 570, and a warning presenter 590. The line-of-sight oscillation detector 510 detects a line of sight and nystagmus (or eye oscillation) of an occupant. The velocity measurer 520 measures the velocity of the vehicle. The vehicle outside imager 530 obtains a range image by capturing the outside of the vehicle by using an imaging means, such as a LIDAR, a stereo camera, or a monocular camera. The "range image" is an image representing depth information with colors, monochrome shades, or the like. As described above, the LIDAR calculates a distance to a target by measuring scattered light resulting from illumination with pulsed laser light. The stereo camera performs capturing with left and right two cameras, thereby generating parallax data of the images and measuring a distance from the lenses to a target. When a monocular camera is used, a distance is calculated from images from multiple viewpoints captured while a camera is being moved, by using a method called Structure from Motion (SfM), for example. In the object oscillation detector 540, from the viewpoint of the occupant and the position of a side window, by assuming that a view area in the outside scene that can be viewed by the occupant through the side window is an object nearest to the vehicle, the view area is estimated. From the velocity of the vehicle obtained from the velocity measurer 520 and the distances to objects outside the vehicle obtained from the vehicle outside imager 530, relative velocities of the objects are calculated, and when the object in the view area forms a pattern in which the object periodically repeats with respect to a traveling direction, it is determined as oscillation and the period is calculated. In general, the maximum distance that can be measured from a range image obtained using an imaging means, such as a LIDAR or a stereo camera, is about 200 meters. Since motion sickness is not likely to occur when an object or scene farther than 200 meters is viewed, it seems that detecting oscillation of an object within the range of measurement with the above means is necessary and sufficient for detection of motion sickness. A periodic change of the object being viewed by the occupant in accordance with movement of the vehicle is detected as oscillation by the above imaging means. The oscillation comparator 550 outputs a difference between the period of the nystagmus and the period at which the object being viewed changes. The period at which the object being viewed changes is, for example, the period at which poles or the like placed at regular intervals on the side of the road are observed from the traveling vehicle. The determination information storage 560 stores information for determining whether the period of the nystagmus can lead to motion sickness. In the motion sickness determiner 570, when the difference output from the oscillation comparator 550 is less than or equal to a threshold value and the period is greater than or equal to a threshold value in the determination information storage 560, it is determined that following the object outside the vehicle with the eyes can cause optokinetic nystagmus, leading to motion sickness. When it is determined that motion sickness can be caused by looking outside, the vehicle controller 580 blocks the outside scene from entering through the side window by using a light control window and darkening (or smoking) it or by other methods, thereby preventing nystagmus. When it is determined that motion sickness can be caused by looking outside, the warning display 590 issues a warning that suggests looking at a distant object outside the vehicle or looking ahead of the vehicle, through a speaker or display.

Figure 9:
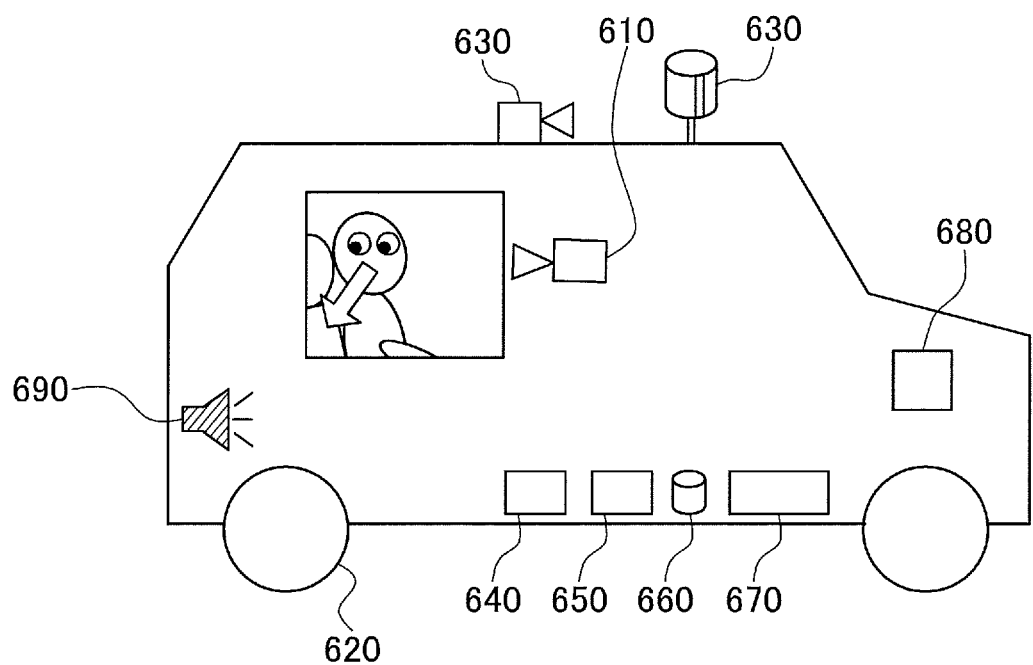
FIG. 9 is an explanatory diagram illustrating an arrangement of elements in a vehicle including the motion sickness prevention device according to the third embodiment of the present invention.

FIG. 9 is an explanatory diagram illustrating an arrangement of elements in a vehicle including the motion sickness prevention device according to the third embodiment of the present invention. In the vehicle illustrated in FIG. 9 are arranged an in-vehicle camera (for detecting a line of sight and nystagmus) 610, a velocimeter 620, a vehicle outside imaging means (LIDAR, camera) 630, an object oscillation detector 640, an oscillation comparator 650, a storage device 660, a determiner 670, a conveyance controller 680, and a speaker 690. The correspondence relationship between the elements in FIG. 9 and the elements in FIG. 8 is as follows: The in-vehicle camera 610 corresponds to the line-of-sight oscillation detector 510. The velocimeter 620 corresponds to the velocity measurer 520. The vehicle outside imaging means (LIDAR, camera) 630 corresponds to the vehicle outside imager 530. The vehicle outside imaging means (LIDAR, camera) 630 can also be referred to as a distance measurer. The object oscillation detector 640 corresponds to the object oscillation detector 540. The oscillation comparator 650 corresponds to the oscillation comparator 550. The storage device 660 corresponds to the determination information storage 560. The determiner 670 corresponds to the motion sickness determiner 570. The conveyance controller 680 corresponds to the vehicle controller 580. The speaker 690 corresponds to the warning presenter 590.

The in-vehicle camera 610 is a device that obtains line-of-sight oscillation of an occupant, which is a detection target, by imaging the occupant. Here, among line-of-sight oscillations, nystagmus is detected. The in-vehicle camera 610 is connected to the oscillation comparator 650.

The velocimeter 620 is a device that measures the velocity of the vehicle. The vehicle velocity is used when an object oscillation is calculated. The velocimeter 620 is connected to the object oscillation detector 640.

The vehicle outside imaging means 630 is one or more distance sensors located inside or outside the vehicle. Each distance sensor is a device, such as a LIDAR, a stereo camera, a monocular camera, or a radar, capable of measuring distance. The distance sensors measure distances to objects located around and outside the vehicle, and are used for determining an object being viewed.

The object oscillation detector 640 determines an object being viewed by the occupant from the vehicle velocity, the distances to the objects outside the vehicle, and the direction of the line of sight of the occupant, and detects, as oscillation, the period at which the object being viewed changes.

The oscillation comparator 650 calculates and outputs a difference between the period of the nystagmus of the occupant detected by the in-vehicle camera 610 and the period detected by the object oscillation detector 640.

When the output of the oscillation comparator 650 is less than or equal to a threshold value, the determiner 670 compares the period of the nystagmus with a threshold value stored in the storage device 660 and determines whether the nystagmus has a period that can lead to motion sickness.

When the occupant is in a state where the occupant can develop motion sickness, the vehicle controller 680 blocks the view by means of smoke so that the neighborhood of the vehicle is not visible. Also, the warning presenter 690 issues a visual or audible warning.

As described for the motion sickness estimation method of the first embodiment, a motion sickness estimation device for executing software of a motion sickness estimation method is illustrated by FIG. 3 as in the first embodiment; hereinafter, a process performed by the CPU 11 will be described with reference to FIG. 10.

Figure 10:
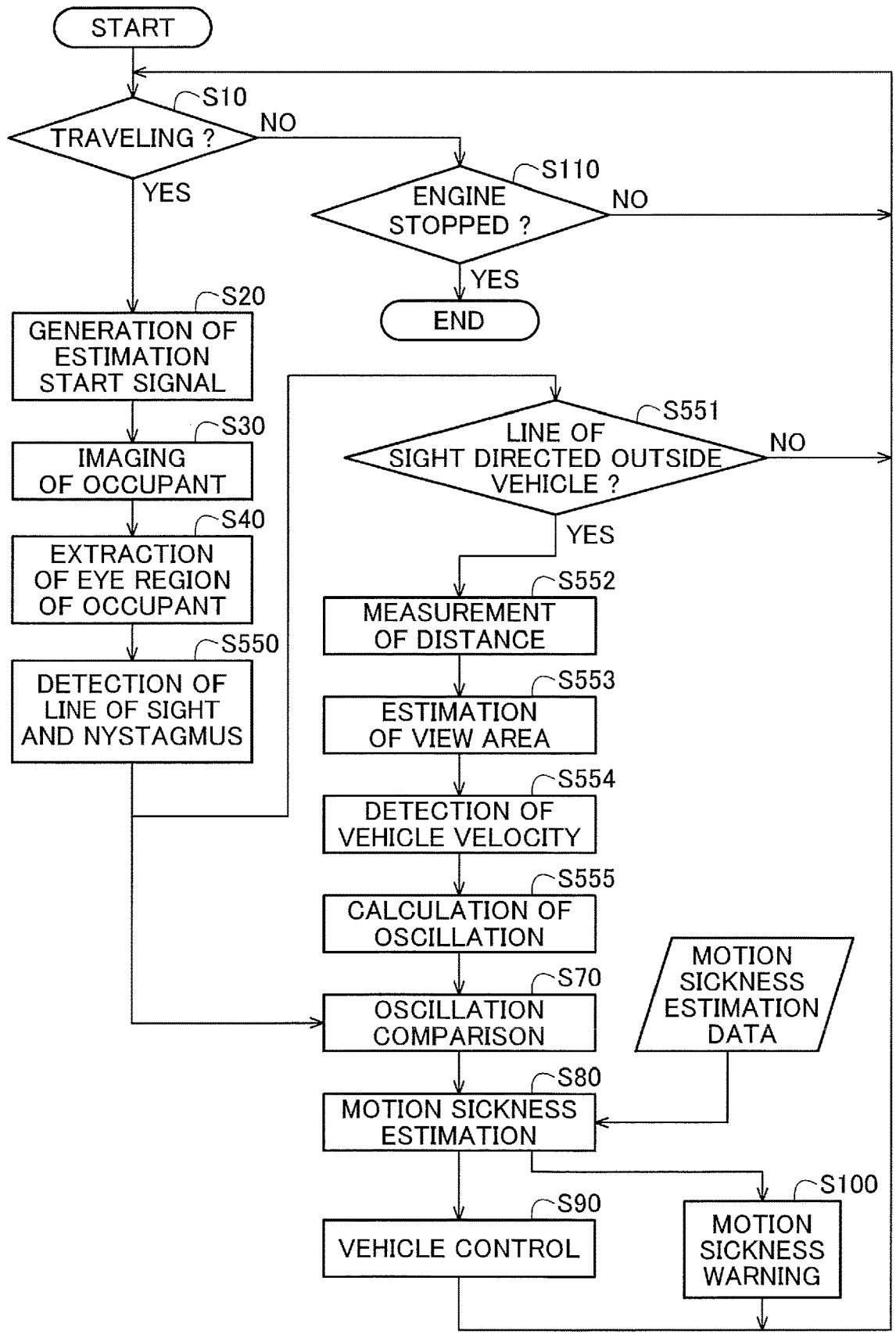
FIG. 10 is a flowchart illustrating a motion sickness estimation method according to the third embodiment of the present invention.

FIG. 10 is a flowchart illustrating a motion sickness estimation method according to the third embodiment of the present invention. The motion sickness estimation method illustrated in FIG. 10 includes a traveling determination step S10, an estimation start signal generation step S20, an imaging step S30, a region extraction step S40, a line-of-sight/nystagmus detection step S550, a line-of-sight determination step S551, a distance measurement step S552, a view area estimation step S553, a vehicle velocity detection step S554, an oscillation calculation step S555, an oscillation comparison step S70, a motion sickness estimation step S80, a vehicle control step S90, a motion sickness warning step S100, and an engine stop determination step S110. For the reference characters of the steps of FIG. 10, the same reference characters are assigned to the steps that perform the same operations as those in the first embodiment and second embodiment.

The traveling determination step S10 determines whether the vehicle is in a traveling state. The determination is made by acquiring determination as to whether the vehicle is traveling from CAN information or the like.

When it is determined that the vehicle is in a traveling state, in the estimation start signal generation step S20, an estimation start signal is generated by a head unit and supplied to the in-vehicle camera 610 and an illumination associated therewith. Next, in the imaging step S30, the in-vehicle camera 610, which has received the supplied signal, images an occupant.

In the region extraction step S40, a device associated with the in-vehicle camera 610 extracts a region of an eye of the occupant. In the line-of-sight/nystagmus detection step S550, the line of sight and nystagmus are detected from the image of the detected eye region. The nystagmus is detected from the angular velocity and period of the eyeball. On the basis of the result of the line-of-sight/nystagmus detection step S550, in the line-of-sight determination step S551, it is determined whether the line of sight is directed outside the vehicle, and the degree of the nystagmus is calculated from the angular velocity of the eyeball.

In the distance measurement step S552, distances between the vehicle and objects therearound are measured.

In the view area estimation step S553, from the viewpoint of the occupant and the position of a side window, by assuming that a view area in the outside scene that can be viewed by the occupant through the side window is the object nearest to the vehicle, the view area is estimated.

In the vehicle velocity detection step S554, the velocity of the vehicle is measured. The velocity of the vehicle is used in determining an object being viewed by the occupant.

In the oscillation calculation step S555, from the distance from the vehicle to an object in the view area estimated in the view area estimation step S553 and the velocity of the vehicle, a relative velocity of the object is calculated, and when the object in the view area forms a pattern in which the object periodically repeats with respect to a traveling direction, it is determined as oscillation and the period is calculated.

In the oscillation comparison step S70, a difference between the period of the nystagmus output from the line-of-sight/nystagmus detection step S550 and the output of the oscillation calculation step S555 is calculated.

In the motion sickness estimation step S80, when the output of the oscillation comparison step S70 is less than or equal to a threshold value, it is determined whether the nystagmus has a period that can lead to motion sickness, by comparing the period of the nystagmus and motion sickness estimation data. When it is determined that motion sickness can be caused, in the vehicle control step S90, a control is performed using a light control window or a sunshade so that the neighborhood of the vehicle is not visible, or in the motion sickness warning step S100, motion sickness is improved by issuing a warning that suggests looking in the distance or ahead of the vehicle. Then, the above flow is repeated by returning to the traveling determination step S10.

The above has described the operations of the motion sickness estimation device and motion sickness estimation method of the third embodiment. The motion sickness estimation device and motion sickness estimation method of the third embodiment provide the same advantages as those of the first embodiment and second embodiment.

Although in the above description, the conveyance in which the occupant is riding has been described as a vehicle, it is not limited to a vehicle, and may be any conveyance, such as a watercraft or an aircraft, that vibrates or oscillates during traveling. Although the vehicle outside imaging means 630 has been described as measuring distances to objects outside the vehicle, it may be an outside imaging means or outside imager that measures distances to objects outside the conveyance.

Although embodiments of the present invention have been described above, the present invention is not limited to these embodiments.

REFERENCE SIGNS LIST 10 motion sickness prevention device
100 motion sickness estimation device
110 line-of-sight oscillation detector
120 object oscillation detector
130 oscillation comparator
140 determination information storage
150 motion sickness determiner
160 vehicle controller
170 warning presenter
210 in-vehicle camera
220 in-vehicle display with acceleration sensor
230 oscillation comparator
240 storage device
250 determiner
260 conveyance controller
270 speaker
30 motion sickness prevention device
300 motion sickness estimation device
310 line-of-sight oscillation detector
320 object oscillation detector
330 oscillation comparator
340 determination information storage
350 motion sickness determiner
360 vehicle controller
370 warning presenter 410 in-vehicle camera (for detecting line-of-sight)
420 in-vehicle camera (for imaging object in line of sight)
430 oscillation comparator
440 storage device
450 determiner
460 conveyance controller
470 speaker
50 motion sickness prevention device
500 motion sickness estimation device
510 line-of-sight oscillation detector
520 velocity measurer
530 distance measurer
540 object oscillation detector
550 oscillation comparator
560 determination information storage
570 motion sickness determiner
580 vehicle controller
590 warning presenter
610 in-vehicle camera (for detecting nystagmus)
620 velocimeter
630 vehicle outside imaging means (LIDAR, camera)
640 object oscillation detector
650 oscillation comparator
660 storage device
670 determiner
680 conveyance controller
690 speaker

The invention claimed is:

1. A motion sickness estimation device comprising:
a line-of-sight oscillation detector to detect oscillation of a line of sight of an occupant by using an imaging device;
an object oscillation detector to detect oscillation of an object located in the line of sight;
an oscillation comparator to calculate an oscillation difference from the oscillation of the line of sight and the oscillation of the object; and
a motion sickness determiner to determine, on a basis of the oscillation difference, whether the occupant is in a motion sickness state.

2. The motion sickness estimation device of claim 1, wherein the object oscillation detector detects the oscillation of the object by measuring an acceleration of the object.

3. The motion sickness estimation device of claim 1, wherein the object oscillation detector detects the oscillation of the object by means of an imaging device.

4. The motion sickness estimation device of claim 1, wherein the motion sickness determiner uses a time integral value of the oscillation difference in the determination.

5. The motion sickness estimation device of claim 1, further comprising a warning presenter to issue a warning when the motion sickness determiner determines that the occupant has a sign of motion sickness.

6. A motion sickness prevention device comprising:
the motion sickness estimation device of claim 1; and
a conveyance controller,
wherein the conveyance controller controls, on a basis of a determination result of the motion sickness determiner, a state of a conveyance in which the occupant is riding to reduce the oscillation difference.

7. A motion sickness estimation device comprising:
a line-of-sight oscillation detector to detect oscillation of a line of sight of an occupant by using an imaging device;
a velocity measurer to measure a velocity of a conveyance in which the occupant is riding;
an outside imager to capture an outside of the conveyance and measure a distance between the conveyance and an object located in the outside;
an object oscillation detector to detect, when the object forms a pattern in which the object periodically repeats with respect to a traveling direction in which the object is captured by the outside imager, a period at which the object repeats with respect to the traveling direction, as oscillation of the object, from the velocity and the distance;
an oscillation comparator to calculate an oscillation difference from the oscillation of the line of sight and the oscillation of the object; and
a motion sickness determiner to determine, on a basis of the oscillation difference, whether the occupant is in a motion sickness state.

8. A motion sickness estimation method comprising:
detecting oscillation of a line of sight of an occupant by using an imaging device;
detecting oscillation of an object located in the line of sight;
calculating an oscillation difference from the oscillation of the line of sight and the oscillation of the object; and
determining, on a basis of the oscillation difference, whether the occupant is in a motion sickness state.

* * * * *